United States Patent [19]
Jeffcoat et al.

[11] 4,333,469
[45] Jun. 8, 1982

[54] BONE GROWTH STIMULATOR

[75] Inventors: Keith W. Jeffcoat, Beacon Hill; Geoffrey G. Wickham, Longueville, both of Australia

[73] Assignee: Telectronics Pty. Ltd., New South Wales, Australia

[21] Appl. No.: 59,443

[22] Filed: Jul. 20, 1979

[51] Int. Cl.³ .............................................. A61N 1/18
[52] U.S. Cl. .................................. 128/419 F; 128/784
[58] Field of Search ............ 128/419 F, 419 B, 419 C, 128/419 P, 419 R, 82.1, 784–786; 174/117 F, 110 PM

[56] References Cited

U.S. PATENT DOCUMENTS

| | | | |
|---|---|---|---|
| 3,082,292 | 3/1963 | Gore | 174/117 F |
| 3,216,424 | 11/1965 | Chardeck | 128/785 |
| 3,376,378 | 4/1968 | Bullock | 174/110 PM |
| 3,659,615 | 5/1972 | Enger | 128/419 P |
| 3,842,841 | 10/1974 | Brighton et al. | 128/419 F |
| 3,943,936 | 3/1976 | Rasor et al. | 128/419 P |
| 4,026,304 | 5/1977 | Levy | 128/419 F |
| 4,041,955 | 8/1977 | Kelly et al. | 128/419 P |
| 4,075,439 | 2/1978 | Smiley | 174/117 F |

FOREIGN PATENT DOCUMENTS

| | | | |
|---|---|---|---|
| 60500 | 3/1975 | Australia | 128/419 F |
| 2552523 | 8/1976 | Fed. Rep. of Germany | 128/419 F |

OTHER PUBLICATIONS

Levy, "Induced Osteogenesis by Electrical Stimulation", vol. 118, No. 9, pp. 1438–1442, Sep. 1971.

*Primary Examiner*—Lee S. Cohen
*Attorney, Agent, or Firm*—Gottlieb, Rackman & Reisman

[57] ABSTRACT

There is disclosed an improved implantable bone growth stimulator having a titanium, bullet-shaped case and pre-stretched helical electrode leads. The leads are sheathed, and the circuitry in the case is potted in silicone elastomer. The shape of the case lends itself to long-bone applications. The potting material is ideal for preventing ionic contamination of the circuit, while the metal case offers the requisite mechanical strength. The shape of the case facilitates removal during an explant procedure, and the pre-stretching of the leads prevents tissue damage at this time. The electrical circuit is a stacked assembly of components without a circuit board, which gives rise to the desired bullet shape of the case.

83 Claims, 10 Drawing Figures

BONE GROWTH STIMULATOR

This invention relates to implantable bone growth stimulators, and more particularly to such devices which are highly reliable in operation and offer additional benefits, e.g., during explant procedures.

It has been known for over twenty years that bone growth, and especially bone-bone fusion, can be accelerated by electrical stimulation. An extensive bibliography on the subject is to be found in the "Premarket Approval Application of Telectronics Pty. Limited for Bone Growth Stimulator 'Osteostim'", dated Jan. 31, 1979 and filed with the Food and Drug Administration. This four-volume document, which is hereby incorporated by reference, describes not only the operation of the bone growth stimulator of our invention, but also detailed step-by-step procedures which may be used in manufacture of the device.

From an "electrical circuit" standpoint, a bone growth stimulator is simply a constant-current source. The device typically includes one anode, and one or more cathodes. The anode may simply be inserted in soft tissue, and the one or more cathode leads are implanted into the bone, using known techniques, in the area of a fracture. The device typically generates a 20-microampere current which stimulates bone growth around the cathode or cathodes. A constant-current source is utilized so that the current does not vary with the impedance between the electrodes. (In the illustrative embodiment of the invention, a constant current is delivered for "load" impedances which may vary between 0 and 100K.) The mechanism by which bone growth is thus stimulated is not completely understood, but numerous experimenters have verified the fact of its existence.

The human body is generally a hostile environment for electronic devices. An unprotected electronic device will be rendered totally inoperative in short order by liquid and ionic contaminants. One of the main reasons for the high cost of implantable pacemakers, for example, is that hermetic-sealing manufacturing procedures are quite complex and costly. But there is no practical alternative; a pacemaker may be vital to life and is usually designed for years of use.

A bone growth stimulator, on the other hand, is not a life-saving device, nor is it expected to function for much longer than six months. It is usually explanted or removed after the desired bone fusion has taken place within this time period. It is therefore not common practice to provide hermetic sealing for bone growth stimulators; the cost cannot be justified. Nevertheless, if precautions are not taken to prevent contamination of the electrical components in the device, it may take only days or weeks before the unit ceases to function. Thus although hermetic sealing may not be cost-justified, it is very important that the "next-best thing" be done to avoid contamination. Prior art bone growth stimulators have not generally offered maximum reliability in this regard.

Prior art bone growth stimulators have also exhibited "mechanical" problems. While size is not usually a critical factor when it comes to pacemakers, that is not always the case with bone growth stimulators. There is just not enough room in a human arm or leg, for example, to implant a bulky device, particularly in small children six months of age and upwards where electrical stimulation may be used as a treatment for congenital pseudarthrosis. Generally speaking, prior art workers have paid little attention to the shapes of bone growth stimulators, and have failed to realize that there may be one particular shape which offers unique advantages—not only for implant purposes, but also when explanting the device after a few months of use.

Still another shortcoming exhibited by some prior art bone growth stimulators is tissue damage which occurs when removing the cathode lead or leads during an explant procedure. The cathode itself cannot be removed from the bone into which it is implanted; bone grows around it. What is sometimes done is to make a separate incision for the sole purpose of cutting the cathode lead at the bone site. An alternative to making an incision, in addition to that required to remove the bone growth stimulator itself, is to pull on the cathode lead; the lead usually breaks at the desired place where it exits the bone. But what then often happens, for reasons to be described below, is that tissues are damaged as the cathode lead is withdrawn from the body. It would be highly desirable during the explant procedure to be able to pull on the cathode lead (without having to make an additional incision), thereby breaking the lead at the point where it exits the bone, and then to withdraw the lead without tearing any tissues in the process.

The aforesaid problems with prior art bone growth stimulators are overcome in accordance with the principles of our invention by incorporating several important features in the design. The most visible of these is the use of a cylindrical bullet-shaped titanium case, with rounded edges, for housing the circuitry. This particular shape is especially well suited for long-bone applications in which there may be little space to accommodate a device. An implanted device should avoid "sharp" corners in its construction, since these are a prime cause of pressure necrosis damage to tissues. The aforesaid bullet-shaped case with rounded ends achieves a maximum radius on all surfaces, consistent with size, and thus minimizes the possibility of pressure necrosis. The rounded edges also facilitate ultimate removal without unnecessary tearing of tissues. The device is preferably fabricated by dispensing with a circuit board, and instead stacking the electrical components along a long axis with the diameter of the device being as small as possible; in fact, the diameter of the device is controlled by the size of the batteries which are utilized and therefore is at a minimum.

Ionic contamination is avoided primarily by first potting the electrical circuit in a silicone elastomer encapsulant, and then placing the cured encapsulated circuit in a two-part bullet-shaped case filled with still more encapsulant. This two-step process, which will be described at length below, is far superior to simply potting the electrical circuit within the case in one step.

The arrangement of the electrical components within the case is also of importance. For example, the batteries are not only placed at the bottom of the case, but they are oriented with their seals facing away from the leads of the transistor employed in the circuit. The mechanical arrangement of the circuit components is designed to minimize the possibility of contamination.

A very important feature of the invention is the cathode lead construction. A conventional titanium helical lead is used, but it is pre-stretched, sheathed in polyethylene, and further has added anti-contaminant protection where it enters the case. The polyethylene sheathing is slippery in body tissue and facilitates removal of the lead without the tearing of tissue. Equally important, because of the pre-stretching of the lead, for reasons to be described below there is little chance of the broken end of the lead being pulled out of its sheathing and contributing to tissue damage as the lead is withdrawn.

There are numerous other features such as the provision of a two-part, screw-threaded case, all of which contribute to the overall reliability and improved use of the device. Further objects, features and advantages of the invention will become apparent upon consideration of the following detailed description in conjunction with the drawing in which:

Figure 1:
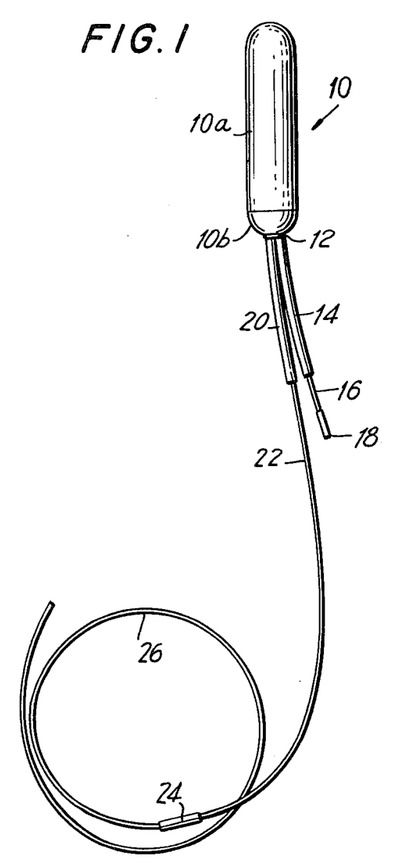
FIG. 1 depicts a completed bone growth stimulator of our invention.

The bone growth stimulator of FIG. 1 consists of a two-part, bullet-shaped titanium housing 10 which contains the circuitry. The housing consists of a main case 10a onto which a cap 10b is screwed. The leads exit a hole at the top of the cap, the case being filled with an encapsulant 12 during the final assembly step, some of the encapsulant being present outside the hole and chemically bonded to the sheathing of the leads.

The anode lead is a pre-stretched titanium helical coil encased in polyethylene tubing 16. The lead is attached to a platinum anode 18 at its tip. The lead is also encased in silicone elastomer tubing 14, in a manner to be described in detail below, at that end which exits cap 10b.

The cathode lead is similarly constructed of pre-stretched helically coiled titanium wire encased in polyethylene tubing 22, with silicone elastomer tubing 20 provided at that end which exits cap 10b. A short section of silicone elastomer tubing 24 terminates the polyethylene tubing 22, and the terminal end 26 of the cathode lead has no tubing whatsoever around it.

Figure 2A:
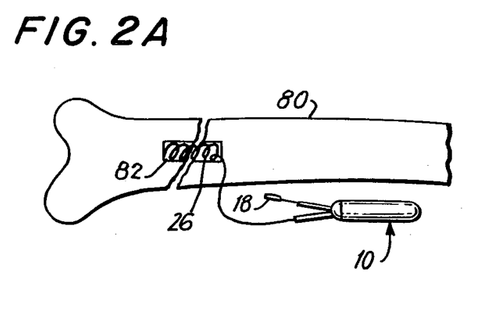
FIGS. 2A and 2B illustrate schematically two implant techniques, both generally known in the art.
Figure 2B:
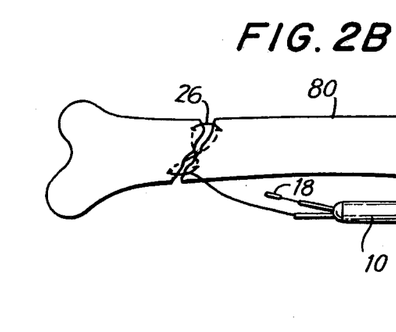

FIGS. 2A and 2B illustrate the manner of use of the bone growth stimulator. The unit is designed to generate a 20-microampere current for up to six months once implanted. The usual implantation technique is shown in FIG. 2A. A block of bone, typically 1 cm wide and 2-3 cm long, is removed from across the fracture site, as shown by the numeral 82. The non-insulated distal end of the cathode lead is formed into a helix by wrapping it tightly in a spiral around a smooth mandril, e.g., the chuck end of a drill bit. The helix begins at the junction of the insulated and non-insulated portions of the lead (24, 26 in FIG. 1). For optimum results, the entire non-insulated portion is implanted into the slot 82. Although the anode 18 may also be placed in the bone, it is preferred to place it in soft tissue.

In the alternative technique of FIG. 2B, two holes are drilled across the fracture site, and the noninsulated end of the cathode lead is threaded through the holes in a figure-eight configuration.

Both implant techniques are well known in the art. The housing 10 of the unit and the anode, when using either technique, may be inserted through a separate incision into an appropriate tissue plane, with the anode preferably being 8-10 cm from the fracture site.

The illustrative embodiment of the invention is designed for "long-bone" fusion and it includes a single long cathode lead. For spinal fusions, a slightly different unit (not shown) should be used. The anode construction is the same as that shown in FIG. 1, but instead of only a single cathode lead, four such leads are used. Each of the leads is comparable to that shown in FIG. 1, except that the noninsulated tip is shorter than tip 26 in FIG. 1. Within the housing, the four ends of the cathode leads are simply joined together. When the posterior approach is used, the implant technique generally involves the drilling of four 1/16" holes in the superior articulate surfaces, adjacent to the inferior articular processes of the vertebra above. The housing and anode are placed into soft tissue by tunneling from the operative side, the housing usually being placed underneath the deep fascia overlying one or other sacrospinalis.

Figure 8:
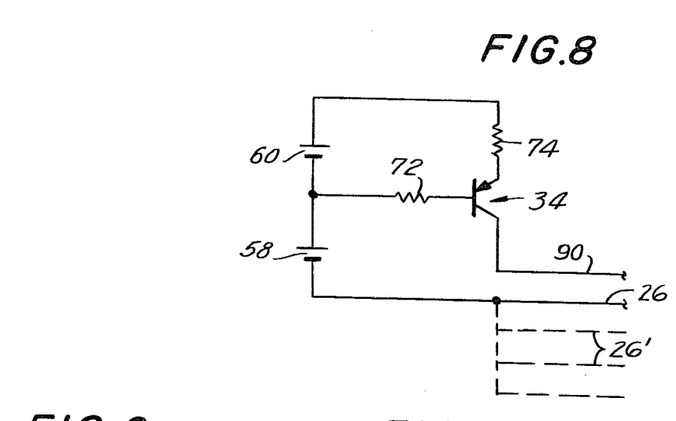
FIG. 8 is a schematic of the electrical circuit.

The constant-current generator itself is shown in FIG. 8, and is a standard circuit. The circuit includes two 1.5-volt silver oxide cells, a 470K resistor 72, a 47K resistor 74, and a BC557 (transistor 34. (Resistor 74 should be larger for smaller currents, if desired.) The anode lead 90 is connected to the collector of the transistor, and the cathode lead 26 is connected to the negative terminal of cell 58. The dashed lines 26' simply indicate the addition of three cathode leads for spinal fusion device.

Figure 3:
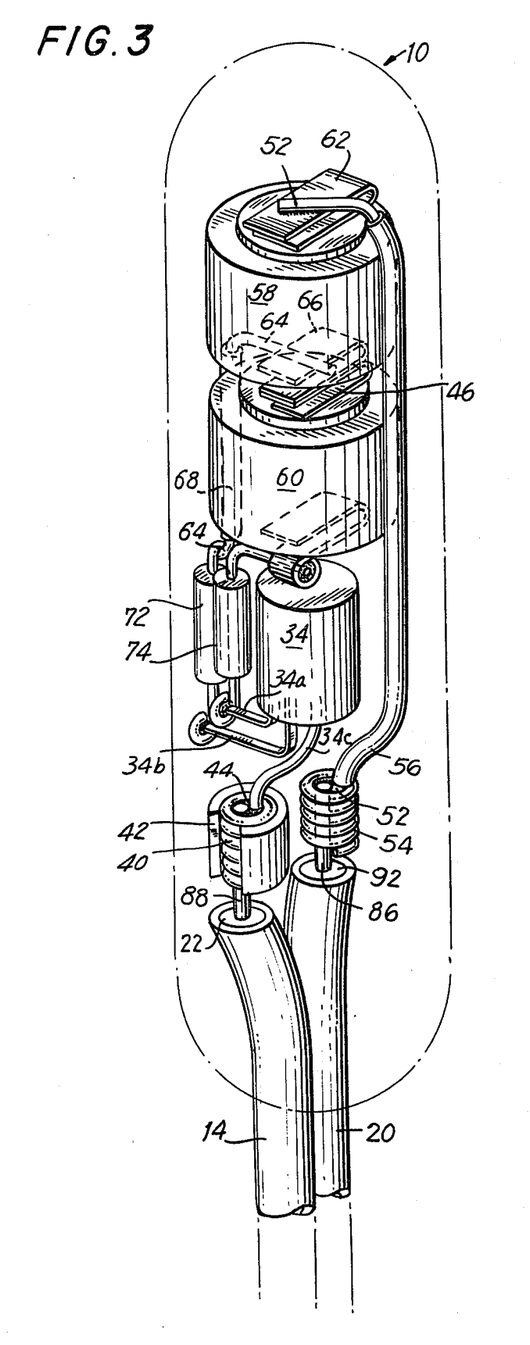
FIG. 3 illustrates the mechanical arrangement of the electrical components, i.e., the stacking configuration.

The physical arrangement of the components is depicted in FIG. 3. Each of batteries 58 and 60 has a pair of tags, such as 62 and 66 associated with battery 58. The tags are bent as shown in the drawing, and tag 66 of battery 58 is first soldered to tag 46 of battery 60. (All solder employed is 60/40 lead/tin solder.) Wire 64 is then soldered to tag 66, this wire having Silastic tubing insulation 68 around it. (All of the silicone elastomers used, both tubing and potting compounds, are available from Dow Corning.) Similarly, wire 52, with silicone rubber insulation 56 around it, is soldered to tag 62. The other end of this wire is soldered to the cathode lead pin 86, as will be described below.

The other end of wire 64 is soldered to one end of resistor 62, and one end of resistor 74 is soldered to the bottom tag on battery 60. The other ends of resistors 72 and 74 are connected respectively to the base terminal 34b and the emitter terminal 34a of transistor 34. The collector terminal 34c is soldered to the anode lead pin 88.

The anode and cathode lead constructions will be described in detail below, but FIG. 3 illustrates the ends of the leads within the housing 10 (the housing being shown in phantom lines). A tinned copper pin 88 is enclosed by silicone rubber tubing 14, with the end of the tubing being sealed with Silastic adhesive 22 (medical grade, Type A, from Dow Corning). Similarly, tinned copper pin 86 exits silicone rubber tubing 20, the end of the tubing being sealed with silicone rubber adhesive 92. Pin 88 is secured to transistor lead 34c by placing a solder coil 40 around them, then soldering the connection, and finally crimping the solder coil (for added mechanical strength), the solder itself being shown by the numeral 44. A similar solder coil 54 is used in the same way to join pin 86 and wire 52. To insure that the two solder coils do not touch each other and short-circuit the leads, a short section of Silastic tubing 42 is placed around solder coil 40. In the event four cathode leads are used, four pins comparable to pin 86 are placed together with the end of wire 52 within a larger-diameter solder coil 54, and the same procedure is followed.

Figure 4:
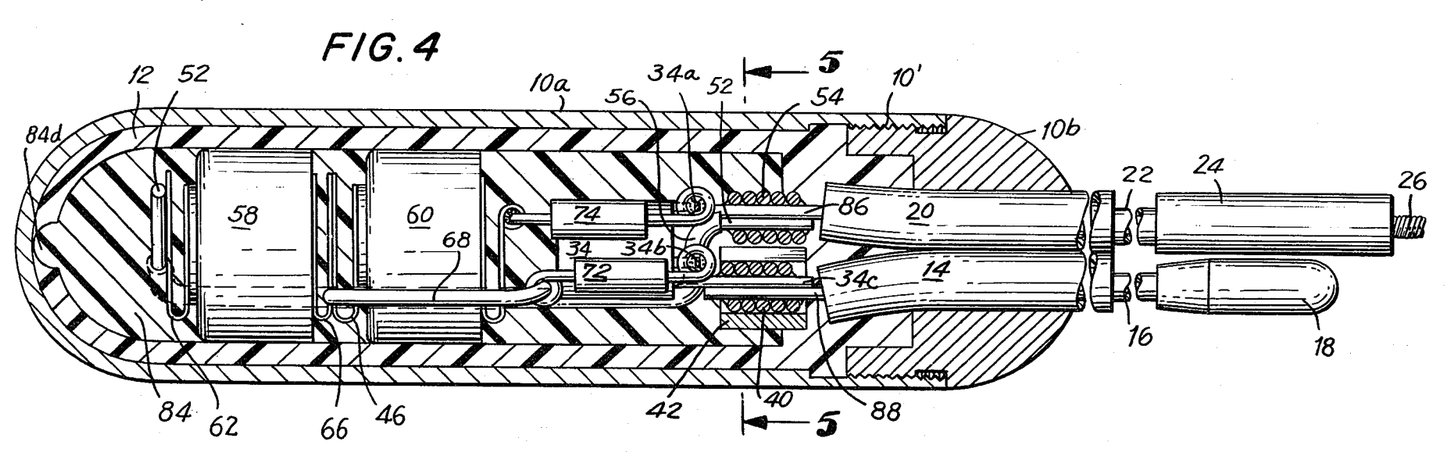
FIG. 4 is a cross-sectional view of the completed device after the final encapsulating step has been taken.
Figure 5:
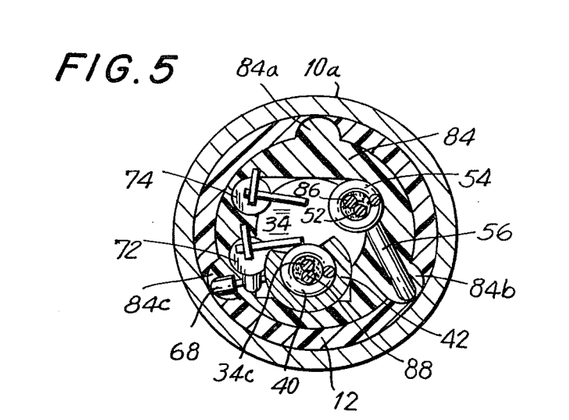
FIG. 5 is a sectional view through the line 5—5 of FIG. 4.

The circuit is then initially potted in silicone elastomer. Dow Corning MDX4-4210 base material is mixed with its curing agent (supplied by Dow Corning with the base material) in a ratio 10:1.4. The mixture is first stirred slowly so as not to introduce excess air while mixing, and a beaker containing the mixture is then placed in a vacuum in order to de-gas the elastomer. The circuit is placed in a mold partially filled with the elastomer, and additional elastomer is then injected into the top of the mold to a point at which the solder coils 40, 54 are covered almost to the top. The shape of the mold and the resulting potting configuration can be best appreciated from FIGS. 4 and 5, the first "pot" being shown by the numeral 84. Referring to FIG. 4, it will be understood that with battery 58 being inserted at the bottom of the mold, the mold is filled with elastomer 84 almost to the top of the two solder coils. Also as shown in FIG. 4, a small nipple 84d is formed at the bottom. FIG. 5 depicts three vertical ribs 84a–84c which are also formed. It should be noted that wires 52 and 64, insulated by silicone rubber tubing 56 and 68, are actually contained within two of the three ribs. The ribs are necessary for reasons to be described below, and by placing the wires in the ribs the diameter of the overall configuration can be made as small as possible. (The wires are insulated with Silastic tubing to insure that they are not exposed at the extreme tips of respective ribs when the potting operation is complete.)

The potted circuit is cured in an oven held at 40° C. for at least 12 hours. It is then examined for air bubbles and discarded if any air bubbles can be seen. The two-step potting process, the second step of which will now be described, is employed primarily so that the intermediate air-bubble check can be performed.

The same silicone elastomer is used in the second potting step. Case 10a is held upright and half-filled with the potting compound. Cap 10b is then slipped over the electrode leads and partially filled with potting material. As the initially potted circuit is slipped down into the case, cap 10b is screwed onto the top of the case, internal threads 10' (FIG. 4) serving to attach the cap to the case. Due to the provision of the three ribs 84a–84c and the nipple 84d in the initial potting, the potting mixture 12 which is initially at the bottom of the case flows upwardly as the circuit is slipped in. Some of the material will exit the hole in the cap, as shown by the numeral 12 in FIG. 1, and any excess is wiped away. If there is insufficient material, then additional resin is inserted with use of a syringe through the hole in the cap. The case is then placed in a curing oven as in the first potting step. Although the reasons for employing these particular steps will be described below, it should be noted at this point that the silicone elastomer bonds to the silicone rubber tubing 14 and 20 (FIG. 4), in order to make as effective a water barrier as possible.

Thus far it has been assumed that the electrode leads are pre-formed before their pins 86 and 88 are soldered to wire 52 and transistor terminal 34c. The pre-forming of the electrode leads will now be described.

Figures 6, 7, 9:
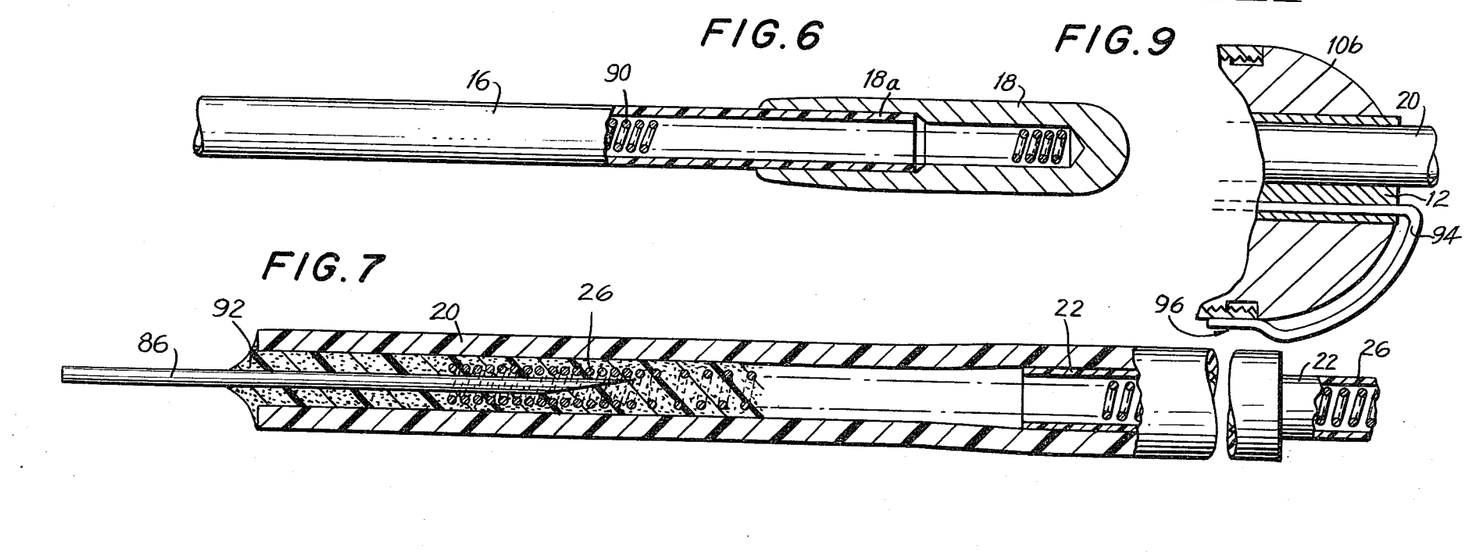
FIG. 6 is a sectional view showing the anode construction.
FIG. 7 is a sectional view showing a portion of the cathode lead.
FIG. 9 depicts an alternative construction in which the titanium case functions as a partial anode.

Titanium helical leads have been used in the prior art. But in accordance with the principles of our invention, the helical leads are pre-stretched past the point at which they would return to their initial positions if released. To make the anode, a 35-mm length of helix is cut, as is a 30 mm length of tinned copper wire. An oblique cut is made at one end of the wire for insertion into an end of the helix. The helix is rotated around the wire and in effect is screwed on it for a length of 5 mm. The free end of the wire is held, as is the free end of the helix, and the helix is stretched until its length has doubled. A 50-mm length of polyethylene tubing is then slipped over the assembly, leaving 15 mm of the helical lead exposed between the end of the polyethylene tubing and the copper wire. Although FIG. 7 depicts the cathode lead construction, at that end of the anode lead which enters the cap, the construction is the same, and thus FIG. 7 illustrates the construction just described. It will be noted that the left end of helical lead 26 is not stretched, and that copper pin 86 is "screwed" into the end of the helix. To the right of the pin, the helix is stretched, and polyethylene tubing 22 covers it. From the left end of the polyethylene tubing to the left end of the helix, the distance is about 15 mm.

A 40-mm length of silicone rubber tubing 20 is then cut and placed over the wire 86 end of the assembly, and onto the polyethylene tubing. This silicone rubber tubing is pushed onto the lead until only about 5 mm separates the left end of the helix and the left end of tubing 20. The "free" space in the silicone rubber tubing is then filled with Silastic adhesive, this step being accomplished with the use of a syringe. The adhesive is then cured in a humidifier for at least twenty-four hours at a relative humidity of 75%. Pin 86 is cut to expose 5 mm, it being this exposed end of the pin which is attached by solder coil 54 to wire 52. The left ends of the anode and cathode leads (FIGS. 6 and 7) are identical in construction.

The right end of the anode lead assembly is shown in FIG. 6. The anode lead helix is designated by the numeral 90 and its polyethylene tubing by the numeral 16. The tubing is cut at the right end at a point which leaves 3 mm of the helix exposed. Referring to FIG. 6, platinum tip 18 is then mounted on the exposed end of the helix. The platinum tip includes an enlarged opening 18a into which the polyethylene tubing is inserted. The tip is permanently secured to the lead by swaging or crimping.

As for the cathode lead, referring to FIGS. 1 and 4, polyethylene tubing 22 exits silicone rubber tubing 20 just as tubing 16 exits tubing 14. But the polyethylene tubing 22 does not extend all the way to the end of the cathode helix lead. Instead, the end of the helix 26 is exposed as depicted in FIG. 1. At the termination of the polyethylene tubing, a short section of silicone rubber tubing 24 is partially placed over it, and the area between the tubing and the helix is filled with Silastic adhesive, much as Silastic adhesive 92 is shown for this purpose in FIG. 7.

The original length of the cathode helix is 178 mm. After pin 88 is screwed into it, the helix is stretched to a length of 410 mm. The polyethylene tubing 16 which is employed has a length of 135 mm, and tubing 24 (FIG. 1) has a length of 40 mm. When it is inserted on the polyethylene tubing, about 5 mm of the silicone rubber tubing should be left exposed over helical lead 26 for application of the adhesive. In the case of cathode lead assemblies employed in bone growth stimulators used for spinal fusions, the original length of each helix is 80 mm and it is stretched to 180 mm. The polyethylene tubing has a length of 135 mm, but in all other respects the construction is the same.

In a unit designed for spinal fusion, each of the four cathodes may have a titanium tip, constructed like the anode shown in FIG. 6. For spinal fusions, it is convenient to drill holes and to insert the tips, rather than bare wires, to establish a friction fit.

It is to be expected that in the manufacture of the device, rigorous procedures will be employed to insure reliability. Generally speaking, the techniques which have been developed to insure the reliability of pacemakers can be employed in constructing bone growth stimulators. For example, after stacking the electrical components and soldering them together, and before the assembly is potted, the unit may be placed in an ultrasonic cleaner filled with Freon. Also, detailed records should be kept along every step of the manufacturing process so that in the event a unit fails to function, the cause can be identified and corrected.

The reason for using a titanium case is that titanium not only provides mechanical strength but it is probably the best tolerated implant metal. (In actual practice, titanium alloys, having at least 90% titanium by weight, can be employed. Stainless steel or cobalt-chrome may also be employed, but these are less desirable.) For the same reason, titanium leads are used. Also, the cathode remains in the bone after explant, and it has been found that titanium is the metal best tolerated by bone. A titanium lead is used despite the fact that its electrical characteristics change as its surface oxidizes, and titanium is not a recognized lead material. Another advantage of using a titanium anode lead is that if a hole develops in the surrounding polyethylene tubing, there is no significant current bleed because of the oxide layer which develops on the surface of the titanium lead. The anode itself must be capable of discharging ions; because the surface of titanium oxidizes if titanium is used as the anode material it may lose its ability to discharge ions. For this reason, a platinum anode is used even though it is more expensive. In this regard, reference should also be made to FIG. 9. Instead of using a titanium helical lead terminating in a platinum tip for the anode, a platinum wire 94 (used instead of pin 88) exits the case, and this wire is bent back and soldered to the titanium case, as shown by the numeral 96. This titanium case, by itself, cannot function properly as an anode because an oxide forms on it and limits the current to levels below 20 ua. But placing a platinum spot on the titanium case improves the anode capability of the case. Thus by spot welding platinum wire 94 to the titanium case, the entire case contributes to the anode function, not to mention that the platinum wire also serves in this capacity (and continues to do so even should the spot weld break). The platinum wire need not be insulated, since the silicone elastomer potting compound in the vicinity of the hole in the cap bonds to it and establishes an adequate water barrier. In all other respects, the device of FIG. 9 is the same as that shown in the other figures. (Instead of using a platinum wire 94, a platinum ring, plate or strip can be employed. Also, platinum alloys may be used, e.g., platinum-iridium; the term "platinum" in the claims includes alloys having at least 90% platinum by weight.)

With a description of the unit in mind, as well as the more important manufacturing steps, the advantages of the invention can now be appreciated.

In prior art bone growth stimulators, helical titanium leads were used and they were covered with silicone rubber tubing all along their length (to the extent that polyethylene tubing is employed in the invention). Polyethylene is a better material to employ because it is stronger; also, it is more "slippery" and facilitates removal of the leads, especially the cathode lead or leads, during explant—it is a relatively simple procedure to pull the polyethylene-sheathed leads without tearing tissue. The strength of polyethylene compared with silicone rubber has the additional advantage that it will not break during explant. When silicone rubber was used in the prior art it would sometimes break and expose the electrode conductor which in turn would damage the surrounding tissue. However, polyethylene does not adhere to the silicone elastomer potting material, and thus water-tight seals are difficult to achieve with this material. The problem is avoided by using short sections of silicone rubber tubing 14 and 20 (FIGS. 4 and 7). The silicone rubber tubing adheres to the potting compound and forms an ideal seal during the potting process. Referring to FIG. 7, the Silastic adhesive 92 adheres not only to the silicone rubber tubing 20, but also to the tinned copper pin 86. Consequently, while fluid may ingress between the polyethylene and silicone rubber tubings (right side of FIG. 7), such fluid meets a solid barrier at the left end consisting of the silicone rubber tubing 20, Silastic adhesive and pin 86, with the silicone rubber tubing 20 making a comparable ideal seal with the silicone elastomer potting compound in the housing. The silicone elastomer encapsulent does not prevent water vapor from entering, but water vapor does not create short circuits. The danger is from ionic contaminants in water, and they are blocked. Although there is only an interference fit between the rigid end of the silicone rubber tubing 20 (FIG. 7) and the polyethylene tubing 22, this interference fit is not the moisture barrier which is relied upon.

Very important is the fact that the electrode leads, and especially the cathode lead or leads, are pre-stretched. During an explant procedure, what is often done is simply to pull on the cathode lead in order to break the lead right at the bone. (The weakest point in the lead is where there is no sheathing—at the bone.) But what has often happened in the prior art is that in the process of withdrawing the cathode lead, the broken end of the lead is not always drawn along with its sheathing (silicone rubber in the prior art, polyethylene in the invention), and this is especially true during the initial pulling. The polyethylene tubing can ride over an unstretched helical lead as the tubing is pulled, and the helical lead can stretch, with a good deal of it being pulled out of the distal end of the polyethylene tubing. As the overall assembly is withdrawn, the "loose" end of the lead may cause tissue damage because it does not slide through tissue as smoothly as does the polyethylene tubing. But by pre-stretching the lead, further stretching is unlikely to occur. In accordance with the principles of our invention, the cathode helical lead is pre-stretched to the point that it stretches (without breaking) by no more than 5%, and preferably no more than 2%, when it is subsequently pulled.

Helical leads are preferred because of their flexibility. But if a lead is constructed of a multiplicity of thin straight wires (a multiplicity being used instead of a single thicker wire for increased flexibility), then once again the wires should not stretch by more than 5% during explant. The three basic requirements of the cathode lead are that it be flexible so that it can be placed in the bone as desired, that it be durable, and that it not leave the polyethylene tubing to any significant degree when the latter is pulled during explant.

The two-step potting process is of considerable importance. It might be though that a single step would be sufficient—filling the case with the compound, and sliding the electrical assembly down into the case. But it is not. One of the most important objectives is to completely fill the case so that there are as few voids as possible—voids can result in the collection of fluids since while all plastics are permeable to water vapor, the vapor can actually condense into liquid only at the voids (it is liquids which create short circuits, not vapors). The problem with the single-step approach is that there is no way to insure that voids have not formed near the electrical components. By potting in two steps, however, the inner assembly can be visually inspected for voids.

Nor is it feasible to pot the assembly in the shape of the housing, inspect it, and then insert it. All voids should be avoided in the housing and a sufficiently thick potted assembly which could accomplish this could not be slipped easily into the housing. For this reason, the potting is done in two steps, with the first step insuring that there are no voids in the immediate vicinity of the circuit components, and the last step insuring that the case is completely filled (hopefully with no voids, but with the least dangerous ones if they do exist), with tight contact being made with the inner surface of the case. In this regard, the importance of ribs 84a–84c (FIG. 5) as well as nipple 84d (FIG. 4) should be appreciated. These elements permit the Silastic potting compound to flow around the initially potted assembly when it is inserted in the case, while at the same time centering the circuit assembly within the case. (Centering is important because some minimal Silastic separation is desired between every electrical component and the case, just in case water does penetrate along the inside surface of the case.)

As an added precaution, before actually potting the electrical assembly, blobs of silicone elastomer may be put over the transistor leads and everywhere else where the existence of air bubbles might be disastrous by giving rise to tracking of body fluids, e.g., on all resistor leads.

The lack of a printed circuit board and the stacking of the electrical components allow a bullet-shaped titanium case to be employed. To avoid problems of placement in long bones, the bullet shape is ideal. The length of the unit should be at least twice its diameter. (Very short lengths may be obtainable if the discrete elements are substituted by an integrated circuit.) Reference to FIG. 4 verifies that the diameter of the case is determined by the diameter of the batteries, and that the stacking arrangement employed therefore produces the smallest possible diameter. Reference to FIG. 5 also reveals that a minimum width is achieved by placing the two wires which are connected to the batteries in two of the side ribs. Every millimeter that the diameter of the unit is made smaller reduces the possibility of pressure necrosis.

It should also be noted that both ends of the case are rounded and that there are no sharp edges. It is especially important that the end of the case opposite the leads be so rounded since it is this end which is pulled out first during the explant procedure. The unit is covered with a cocoon of fibrous tissue by the time it is to be withdrawn. The cylindrical shape with a rounded end insures that there is a minimum tearing of tissue during the explant procedure.

In accordance with the principles of our invention, the height of the cylindrical housing should be at least two times its diameter.

In the prior art, not only were cylindrically-shaped units not employed (conventional rectangular-shaped units have been the norm), but the cases used were not made of metal, nor was there a screw fit between prior art cases and their caps. The use of a metal case and a threaded cap, however, are both important. In the prior art, epoxy potting compounds were used. Epoxy is strong and a surgeon could grip an epoxy case with forceps during the implant procedure; but epoxy materials are not the best choice for long life because they produce ionic and/or polar by-products when exposed to water vapor and these by-products can short the circut elements. Silicone elastomers, on the other hand, are all chemically much more stable barriers to water vapor but they are mechanically weak and can be damaged when gripped by forceps. That is why a silicone elastomer potting compound is used, together with a metal case—for the greatest strength and for excellent resistance to water vapor. Another advantage of the titanium case over prior art plastics is that the color of the case stands out better and makes removal of the unit easier.

Any potting compound can swell as it absorbs water vapor, and in the prior art caps have been known to pop off. The use of a metal case with a threaded cap insures that this does not happen. At worst, some of the potting compound simply oozes out of the hole in the cap. Out-gasing of the batteries in the prior art also contributed to popping caps. This problem does not exist in our invention since silicone elastomers allow any gases from the batteries to diffuse through them and exit the hole in the cap.

Silicone elastomer materials are not the only potting compounds which can be employed, for example, parafin wax may be used. In general, the potting compound should allow out-gasing, be impervious to liquids, nonproductive of ionic and polar molecules, and allow the second potting step to result in an adhesion not only to the first potting assembly but also to the metal case. Silastic materials are ideal in this regard because they adhere to titanium. The bond which forms insures that there is minimum space between the potting encapsulant and the case where bacteria could have become entrapped. Also, a most likely path for the ingress of water would be along the case wall, and a tight bond prevents this from happening.

When performing the second potting step, some of the Silastic material is placed in the cap, as described above. This results in a layer of the material between the screw threads—still further protection against liquid penetration.

Reference to FIG. 4 reveals another important property of the finished unit. There is at least one centimeter between every electrical component and the point at which the leads exit the case through the hole in the cap. One of the most likely water flow paths is along the electrode leads, through a possible defect in the Silastic fillers such as 92 in FIG. 7. Any such water flow must travel through at least one centimeter of the potting compound before reaching one of the circuit components. The threaded cap also makes it more difficult for the ingress of water, as opposed to the snap-on caps of the prior art.

All batteries have a tendency to leak electrolyte. Each of the batteries employed in the invention has a seal around its negative terminal, and this is the spot most prone to exhibit leaking. Referring to FIG. 4, it is to be noted that the negative terminals are facing away from the electrical components, and the transistor leads are similarly facing away from the batteries. This maximizes the path between the most probable source of a short circuit (a leaking electrolyte) and the most dangerous short circuit—between the emitter and collector of the transistor.

Although the invention has been described with reference to particular embodiments, it is to be understood that these embodiments are merely illustrative of the application of the principles of the invention. For example, in the circuit of FIG. 9 the platinum wire 94 could be connected internally to the titanium case. Thus it is to be understood that numerous modifications may be made in the illustrative embodiment of the invention and other arrangements may be devised without departing from the spirit and scope of the invention.

What we claim is:

1. An implantable bone growth stimulator comprising a case made of at least 90% titanium, a current source in said case, and anode and at least one cathode leads electrically connected to said current source and exiting said case; characterized by said case having a cylindrical cross-section and a length which is at least two times greater than its diameter, said anode lead being made of platinum, being bent back where it exits said case, and being electrically connected to said case.

2. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said current source being a boardless circuit whose components are stacked along the length of said case, said circuit including at least one transistor and at least one battery having a seal therearound, the leads of said at least one transistor and the seal of said at least one battery being disposed at and facing opposite ends of said case, said at least one battery being oriented with its axis co-extensive with the axis of said case, with the largest diametrical dimension of said stacked circuit being essentially that of said at least one battery, said stacked circuit being potted within a silicone elastomer which fills said case, said silicone elastomer potting consisting of a first pot completely enclosing said stacked circuit and a second pot completely filling the space between said first pot and said case.

3. An implantable bone growth stimulator in accordance with claim 2 wherein said first pot includes a plurality of ribs along the exterior thereof for facilitating the formation of said second pot within said case.

4. An implantable bone growth stimulator in accordance with claim 3 wherein said stacked circuit includes at least one wire connected to a battery terminal and being partially disposed in one of said ribs.

5. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said current source being a boardless circuit whose components are stacked along the length of said case, said circuit including at least one transistor and at least one battery having a seal therearound, the leads of said at least one transistor and the seal of said at least one battery being disposed at and facing opposite ends of said case, said at least one battery being oriented with its axis co-extensive with the axis of said case, with the largest diametrical dimension of said stacked circuit being essentially that of said at least one battery, said stacked circuit being potted within a silicone elastomer which fills said case, said at least one cathode lead being sheathed in polyethylene, and further including silicone elastomer tubing covering that end of the polyethylene sheath which is adjacent to said case, extending into said case, and being bonded to the surrounding silicone elastomer pot which fills said case.

6. An implantable bone growth stimulator in accordance with claim 5 wherein said at least one cathode lead is coated with silicone elastomer within said tubing adjacent to said end of said polyethylene sheath.

7. An implantable bone growth stimulator in accordance with claim 6 wherein said at least one cathode lead stretches by no more than 5% when it is pulled before it breaks.

8. An implantable bone growth stimulator in accordance with claim 7 wherein said at least one cathode lead is in the shape of a pre-stretched helix.

9. An implantable bone growth stimulator comprising a case having a screwthreaded cap, a current source in said case, and anode and at least one cathode leads electrically connected to said current source and exiting said case; characterized by said case being made of metal, and having a cylindrical cross-section and a length which is at least two times greater than its diameter, said current source being potted in silicone elastomer material within said case, some of said material being disposed in the thread of said cap.

10. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said current source being potted in silicone elastomer material within said case, with at least one centimeter of said material separating every electrical component in said current source from the points at which said leads exit said case.

11. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said current source being potted in a material which adheres to the inside wall of said case, allows out-gasing and is impervious to liquids and ionic and polar molecules, with at least one centimeter of said material separating every electrical component in said current source from the points at which said leads exit said case.

12. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said current source being potted within a silicone elastomer which fills said case, said silicone elastomer potting consisting of a first pot completely enclosing said current source and a second pot completely filling the space between said first pot and said case.

13. An implantable bone growth stimulator in accordance with claim 10 wherein said first pot includes a plurality of ribs along the exterior thereof for facilitating the formation of said second pot within said case.

14. An implantable bone growth stimulator in accordance with claim 13 wherein said current source includes at least one wire connected to a battery terminal and being partially disposed in one of said ribs.

15. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said current source being potted within a silicone elastomer which fills said case, said at least one cathode lead being sheathed in polyethylene, and further including silicone elastomer tubing covering that end of the polyethylene sheath which is adjacent to said case, extending into said case, and being bonded to the surrounding silicone elastomer pot which fills said case.

16. An implantable bone growth stimulator in accordance with claim 15 wherein said at least one cathode lead is coated with silicone elastomer within said tubing adjacent to said end of said polyethylene sheath.

17. An implantable bone growth stimulator in accordance with claim 16 wherein said at least one cathode lead stretches by no more than 5% when it is pulled before it breaks.

18. An implantable bone growth stimulator in accordance with claim 17 wherein said at least one cathode lead is in the shape of a pre-stretched helix.

19. An implantable bone growth stimulator comprising a case, a current source in said case, and anode and at least one cathode leads electrically connected to said current source and exiting said case; characterized by said case being made of metal, and having a cylindrical cross-section and a length which is at least two times greater than its diameter, said at least one cathode lead being covered with a plastic sheath, and said at least one cathode lead stretching by no more than 5% when it is pulled before it breaks.

20. An implantable bone growth stimulator in accordance with claim 19 wherein said at least one cathode lead is in the shape of a pre-stretched helix.

21. An implantable bone growth stimulator in accordance with claim 20 wherein said plastic sheath is made of polyethylene.

22. An implantable bone growth stimulator in accordance with claim 19 wherein said plastic sheath is made of polyethylene.

23. An implantable bone growth stimulator comprising a case, a current source in said case, and anode and at least one cathode leads electrically connected to said current source with at least said one cathode lead exiting said case; characterized by said case being made of a material which is at least 90% titanium, said anode lead being electrically attached to said case and said case having platinum on the exterior thereof.

24. An implantable bone growth stimulator comprising a case, a current source in said case, and anode and at least one cathode leads electrically connected to said current source with at least said one cathode lead exiting said case; characterized by said cathode lead and said case being made of materials which are at least 90% titanium, said anode lead being made of platinum, and said anode lead being electrically attached to said case, said current source being potted within a silicone elastomer which fills said case, said silicone elastomer potting consisting of a first pot completely enclosing said current source and a second pot completely filling the space between said first pot and said case.

25. An implantable bone growth stimulator comprising a case, a current source in said case, and anode and at least one cathode leads electrically connected to said current source with at least said one cathode lead exiting said case; characterized by said cathode lead and said case being made of materials which are at least 90% titanium, said anode lead being made of platinum, and said anode lead being electrically attached to said case, said current source being potted within a silicone elastomer which fills said case, said at least one cathode lead being sheathed in polyethylene and further including silicone elastomer tubing covering that end of the polyethylene sheath which is adjacent to said case, extending into said case, and being bonded to the surrounding silicone elastomer pot which fills said case.

26. An implantable bone growth stimulator in accordance with claim 25 wherein said at least one cathode lead is coated with silicone elastomer within said tubing adjacent to said end of said polyethylene sheath.

27. An implantable bone growth stimulator in accordance with claim 26 wherein said at least one cathode lead stretches by no more than 5% when it is pulled before it breaks.

28. An implantable bone growth stimulator in accordance with claim 27 wherein said at least one cathode lead is in the shape of a pre-stretched helix.

29. An implantable bone growth stimulator comprising a case, a current source in said case, and anode and at least one cathode leads electrically connected to said current source with at least said one cathode lead exiting said case; characterized by said cathode lead and said case being made of materials which are at least 90% titanium, said anode lead being made of platinum, and said anode lead being electrically attached to said case, said at least one cathode lead being covered with a plastic sheath, and said at least one cathode lead stretching by no more than 5% when it is pulled before it breaks.

30. An implantable bone growth stimulator in accordance with claim 29 wherein said at least one cathode lead is in the shape of a pre-stretched helix.

31. An implantable bone growth stimulator in accordance with claim 30 wherein said plastic sheath is made of polyethylene.

32. An implantable bone growth stimulator comprising a case, a current source in said case, and anode and at least one cathode leads electrically connected to said current source with at least said one cathode lead exiting said case; characterized by said cathode lead and said case being made of materials which are at least 90% titanium, said anode lead being made of platinum, and said anode lead being electrically attached to said case, said anode lead exiting said case, being bent back, and being attached to the outside of said case.

33. An implantable bone growth stimulator comprising a case; a current source in said case; said current source being potted in a material which adheres to the inside wall of said case, allows out-gasing and is impervious to liquids and ionic and polar molecules; and anode and at least one cathode leads electrically connected to said current source and exiting said case; characterized by said current source including at least one transistor and at least one battery having a seal therearound, with the leads of said at least one transistor and the seal of said at least one battery being disposed at and facing opposite ends of said case, said current source being potted in silicone elastomer material, with at least one centimeter of said material separating every electrical component in said current source from the points at which said leads exit the case.

34. An implantable bone growth stimulator comprising a case; a current source in said case; said current source being potted in a material which adheres to the inside wall of said case, allows out-gasing and is impervious to liquids and ionic and polar molecules; and anode and at least one cathode leads electrically connected to said current source and exiting said case; characterized by said current source including at least one transistor and at least one battery having a seal therearound, with the leads of said at least one transistor and the seal of said at least one battery being disposed at and facing opposite ends of said case, said current source being potted within a silicone elastomer which fills said case, said silicone elastomer potting consisting of a bubble-free first pot completely enclosing said current source and a second pot completely filling the space between said first pot and said case.

35. An implantable bone growth stimulator comprising a case; a current source in said case; said current source being potted in a material which adheres to the inside wall of said case, allows out-gasing and is impervious to liquids and ionic and polar molecules; and anode and at least one cathode leads electrically connected to said current source and exiting said case; characterized by said current source including at least one transistor and at least one battery having a seal therearound, with the leads of said at least one transistor and the seal of said at least one battery being disposed at and facing opposite ends of said case, said current source being potted within a silicone elastomer which fills said case, said at least one cathode lead being sheathed in polyethylene, and further including silicone elastomer tubing covering that end of the polyethylene sheath which is adjacent to said case, extending into said case, and being bonded to the surrounding silicone elastomer pot which fills said case.

36. An implantable bone growth stimulator in accordance with claim 35 wherein said at least one cathode lead is coated with silicone elastomer within said tubing adjacent to said end of said polyethylene sheath.

37. An implantable bone growth stimulator in accordance with claim 36 wherein said at least one cathode lead stretches by no more than 5% when it is pulled before it breaks.

38. An implantable bone growth stimulator in accordance with claim 37 wherein said at least one cathode lead is in the shape of a pre-stretched helix.

39. An implantable bone growth stimulator comprising a case; a current source in said case; said current source being potted in a material which adheres to the inside wall of said case, allows out-gasing and is impervious to liquids and ionic and polar molecules; and anode and at least one cathode leads electrically connected to said current source and exiting said case; characterized by said current source including at least one transistor and at least one battery having a seal therearound, with the leads of said at least one transistor and the seal of said at least one battery being disposed at and facing opposite ends of said case, said at least one cathode lead being covered with a plastic sheath, and said at least one cathode lead stretching by no more than 5% when it is pulled before it breaks.

40. An implantable bone growth stimulator in accordance with claim 39 wherein said at least one cathode leads is in the shape of a pre-stretched helix.

41. An implantable bone growth stimulator in accordance with claim 40 wherein said plastic sheath is made of polyethylene.

42. An implantable bone growth stimulator in accordance with claim 34 wherein said plastic sheath is made of polyethylene.

43. An implantable bone growth stimulator comprising a case, a current source in said case, and anode and at least one cathode leads electrically connected to said current source and exiting said case; characterized by said current source being completely encapsulated by a bubble-free first pot, with a second pot completely filling the space between said first pot and said case.

44. An implantable bone growth stimulator in accordance with claim 43 wherein said first pot includes a plurality of ribs along the exterior thereof for facilitating the formation of said second pot within said case.

45. An implantable bone growth stimulator in accordance with claim 43 wherein said at least one cathode lead is sheathed in plastic, and further including tubing covering that end of the sheath which is adjacent to said case, extending into said case, and being bonded to the surrounding second pot which fills said case.

46. An implantable bone growth stimulator in accordance with claim 45 wherein said second pot material is a silicone elastomer and said at least one cathode lead is coated with silicone elastomer within said tubing adjacent to said end of said plastic sheath.

47. An implantable bone growth stimulator in accordance with claim 43 wherein said at least one cathode lead stretches by no more than 5% when it is pulled before it breaks.

48. An implantable bone growth stimulator in accordance with claim 47 wherein said at least one cathode lead is in the shape of a pre-stretched helix.

49. An implantable bone growth stimulator in accordance with claim 43 wherein at least one centimeter of potting material separates every electrical component in said current source from the points at which said leads exit said case.

50. An implantable bone growth stimulator comprising a case, a current source in said case, and anode and at least one cathode leads electrically connected to said current source and exiting said case; characterized by said at least one cathode lead being covered with a plastic sheath and stretching by no more than 5% when it is pulled before it breaks.

51. An implantable bone growth stimulator in accordance with claim 50 wherein said at least one cathode lead is in the shape of a pre-stretched helix.

52. An implantable bone growth stimulator in accordance with claim 50 wherein said current source is potted in silicone elastomer material within said case, and at least one centimeter of said material separates every electrical component in said current source from the points at which said leads exit the case.

53. An implantable bone growth stimulator in accordance with claim 50 wherein said current source is potted within a silicone elastomer which fills said case.

54. An implantable bone growth stimulator in accordance with claim 53 wherein the silicone elastomer potting consists of a first pot completely enclosing said current source and a second pot completely filling the space between said first pot and said case.

55. An implantable bone growth stimulator in accordance with claim 53 wherein said at least one cathode lead is sheathed in polyethylene, and further including silicone elastomer tubing covering that end of the polyethylene sheath which is adjacent to said case, extending into said case, and being bonded to the surrounding silicone elastomer pot which fills said case.

56. An implantable bone growth stimulator in accordance with claim 50 wherein said at least one cathode lead is made of a material which is at least 90% titanium by weight.

57. An implantable bone growth stimulator comprising a metal case, a potted current source in said case, and anode and at least one cathode leads electrically connected to said current source and exiting said case; characterized by said case having a cylindrical cross-section and a screw-threaded cap, said cap having a hole through which said leads exit, said case having an end opposite said cap which is rounded, said current source being potted within a first pot of silicone elastomer which completely encloses said current source, and a second pot of silicone elastomer completely filling the space between said first pot and said case.

58. An implantable bone growth stimulator comprising a metal case, a potted current source in said case, and anode and at least one cathode leads electrically connected to said current source and exiting said case; characterized by said case having a cylindrical cross-section and a screw-threaded cap, said cap having a hole through which said leads exit, and said current source being potted in silicone elastomer material within said case, with at least one centimeter of said material separating every electrical component in said current source from the points at which said leads exit the case.

59. An implantable bone growth stimulator comprising a metal case, a potted current source in said case, and anode and at least one cathode leads electrically connected to said current source and exiting said case; characterized by said case having a cylindrical cross-section and a screw-threaded cap, said cap having a hole through which said leads exit, and said current source being potted in a material which adheres to the inside wall of said case, allows out-gasing and is impervious to liquids and ionic and polar molecules, with at least one centimeter of said material separating every electrical component in said current source from the points at which said leads exit the case.

60. An implantable bone growth stimulator comprising a metal case, a potted current source in said case, and anode and at least one cathode leads electrically connected to said current source and exiting said case; characterized by said case having a cylindrical cross-section and a screw-threaded cap, said cap having a hole through which said leads exit, and said at least one cathode lead is covered with a plastic sheath, said at least one cathode lead stretching by no more than five percent when it is pulled before it breaks.

61. An implantable bone growth stimulator in accordance with claim 60 wherein said at least one cathode lead is in the shape of a pre-stretched helix.

62. An implantable bone growth stimulator in accordance with claim 61 wherein said plastic sheath is made of polyethylene.

63. An implantable bone growth stimulator in accordance with claim 60 wherein said plastic sheath is made of polyethylene.

64. An electrode for an implantable bone growth stimulator comprising an electrically conductive lead encased in a plastic sheath, said lead stretching by no more than five percent before it breaks and being implantable in a human body for use with said implantable bone growth stimulator.

65. An electrode in accordance with claim 64 wherein said plastic sheath is made of polyethylene.

66. An electrode in accordance with claim 64 further including a piece of silicone elastomer tubing partially contained on one end of said plastic sheath with said lead extending through said tubing, and silicone elastomer adhesive contained within said tubing around that portion of said lead which extends therethrough.

67. An electrode in accordance with claim 64 wherein said lead is made of a material which is at least ninety percent titanium by weight.

68. An electrode lead for an implantable bone growth stimulator comprising a pre-stretched helical coil encased in a plastic sheath, said coil stretching further by no more than 5% before it breaks.

69. An electrode lead in accordance with claim 68 wherein said plastic sheath is made of polyethylene.

70. An electrode lead in accordance with claim 68 further including silicone elastomer tubing being partially contained on one end of said plastic sheath with said coil extending through said tubing, and silicone elastomer adhesive contained within said tubing around that portion of said coil which extends therethrough.

71. An electrode lead in accordance with claim 68 wherein said helical coil is made of a material which is at least 90% titanium by weight.

72. A method of making an implantable bone growth stimulator comprising the steps of assembling a current source with anode and at least one cathode leads electrically connected thereto, potting said current source so that it is completely encapsulated except for said leads, placing the potted current source in a case with said leads exiting the case and with there being free space between the potted current source and the case, and potting the encapsulated current source with a material which completely fills the free space in said case.

73. A method of making an implantable bone growth stimulator in accordance with claim 72 wherein said case is made of metal and the materials used in both potting steps are silicone elastomers.

74. A method of making an implantable bone growth stimulator in accordance with claim 73 wherein said case has a cylindrical shape, and said current source is assembled as a boardless circuit whose components are stacked so as to fit within said case.

75. A method of making an implantable bone growth stimulator in accordance with claim 74 wherein the encapsulated current source is made with a plurality of ribs along its exterior surface for facilitating the potting thereof in said case.

76. A method of making an implantable bone growth stimulator in accordance with claim 75 wherein prior to at least the last potting step the ends of said leads which are connected to said current source are sheathed in silicone elastomer tubing, and silicone elastomer adhesive is placed around said lead ends within said tubing, the ends of said tubing being potted during at least one of said potting steps.

77. A method of making an implantable bone growth stimulator in accordance with claim 76 wherein said case is at least 90% titanium, and the silicone elastomer used in the last potting step adheres to the inside wall of said case.

78. A method of making an implantable bone growth stimulator in accordance with claim 73 wherein prior to at least the last potting step the ends of said leads which are connected to said current source are sheathed in silicone elastomer tubing, and silicone elastomer adhesive is placed around said lead ends within said tubing, the ends of said tubing being potted during at least one of said potting steps.

79. A method of making an implantable bone growth stimulator in accordance with claim 73 wherein said case is at least 90% titanium, and the silicone elastomer used in the last potting step adheres to the inside wall of said case.

80. A method of making an implantable bone growth stimulator in accordance with claim 72 wherein said case has a cylindrical shape, and said current source is assembled as a boardless circuit whose components are stacked so as to fit within said case.

81. A method of making an implantable bone growth stimulator in accordance with claim 80 wherein the encapsulated current source is made with a plurality of ribs along its exterior surface for facilitating the potting thereof in said case.

82. A method of making an implantable bone growth stimulator in accordance with claim 72 wherein the material used in the last potting step is a silicone elastomer, and prior to at least the last potting step the ends of said leads which are connected to said current source are sheathed in silicone elastomer tubing, and silicone elastomer adhesive is placed around said lead ends within said tubing, the ends of said tubing being potted during at least one of said potting steps.

83. A method of making an implantable bone growth stimulator in accordance with claim 82 wherein said case is at least 90% titanium, and the silicone elastomer used in the last potting step adheres to the inside wall of said case.

* * * * *